US011491048B2

(12) United States Patent
McGregor et al.

(10) Patent No.: US 11,491,048 B2
(45) Date of Patent: Nov. 8, 2022

(54) RADIATIVE WARMING SYSTEM

(71) Applicant: 3M INNOVATIVE PROPERTIES COMPANY, Saint Paul, MN (US)

(72) Inventors: Andrew J. McGregor, West Lakeland, MN (US); Melissa L. Bailey, Cottage Grove, MN (US); Jared J. Balthazor, Linwood Township, MN (US); Melanie L. Collins, Minneapolis, MN (US); Stefan O. Dietrich, Ratingen (DE); Korey W. Karls, Woodbury, MN (US); Matthew T. Scholz, Woodbury, MN (US); Albert P. Van Duren, Stillwater, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 826 days.

(21) Appl. No.: 16/426,257

(22) Filed: May 30, 2019

(65) Prior Publication Data
US 2019/0374375 A1     Dec. 12, 2019

Related U.S. Application Data

(60) Provisional application No. 62/681,735, filed on Jun. 7, 2018.

(51) Int. Cl.
*A61F 7/00*     (2006.01)
*A61B 5/01*     (2006.01)
*H05B 3/00*     (2006.01)

(52) U.S. Cl.
CPC .............. *A61F 7/00* (2013.01); *A61B 5/01* (2013.01); *H05B 3/0085* (2013.01);
(Continued)

(58) Field of Classification Search
CPC . A61B 2562/0271; A61B 5/01; A61B 5/4836; A61B 5/6892; A61F 2007/0088;
(Continued)

(56) References Cited

U.S. PATENT DOCUMENTS

| 4,186,294 | A | * | 1/1980 | Bender | ............... | H05B 3/38 |
| | | | | | | 219/528 |
| 4,913,505 | A | | 4/1990 | Levy | | |

(Continued)

FOREIGN PATENT DOCUMENTS

| CN | 203207205 | 9/2013 |
| GB | 2477926 | 8/2011 |

(Continued)

OTHER PUBLICATIONS

"Electronics/Batteries Thermal Management", Outlast Technologies, [retrieved from the internet on Jul. 22, 2019], URL <http://www.outlast.com/en/end-uses/>, p. 1.

(Continued)

*Primary Examiner* — Tigist S Demie
(74) *Attorney, Agent, or Firm* — Jeffrey M. Olofson

(57) ABSTRACT

Aspects of the present disclosure relate to a warming system. The warming system includes a light device having a light source configured to be positioned proximate to a patient support having a patient support surface. The light source can also be configured to generate infrared radiation. The warming system can also include a flexible sheet having a first side configured to reflect at least some of the generated infrared radiation from the light device toward a portion of the patient support surface.

19 Claims, 6 Drawing Sheets

(52) U.S. Cl.
CPC .............. *A61B 2562/0271* (2013.01); *A61F 2007/0088* (2013.01); *A61F 2007/0095* (2013.01)

(58) Field of Classification Search
CPC ...... A61F 2007/0093; A61F 2007/0095; A61F 2007/0255; A61F 2007/0288; A61F 7/00; A61F 7/02; A61G 13/10; A61G 2210/90; A61N 5/0625; H05B 3/0085
See application file for complete search history.

(56) References Cited

U.S. PATENT DOCUMENTS

| | | | |
|---|---|---|---|
| 4,969,459 | A | 11/1990 | Gusakov |
| 5,817,003 | A | 10/1998 | Moll |
| 6,245,010 | B1 | 6/2001 | Jones |
| 6,351,678 | B1 | 2/2002 | Borders |
| 6,761,682 | B2 | 7/2004 | Goldberg |
| 8,160,717 | B2 | 4/2012 | Ameri |
| 8,812,132 | B2 | 8/2014 | Hendriks |
| 9,615,983 | B2 | 4/2017 | Stryker |
| 9,642,404 | B2 | 5/2017 | Giles |
| 2005/0043776 | A1 | 2/2005 | Purcell |
| 2009/0210025 | A1 | 8/2009 | Ameri |
| 2010/0280581 | A1 | 11/2010 | Cushman |
| 2011/0046433 | A1 | 2/2011 | Khodak |
| 2011/0208275 | A1 | 8/2011 | Schock |
| 2011/0224760 | A1* | 9/2011 | Potter ................. A61F 7/0097 607/104 |
| 2012/0284918 | A1 | 11/2012 | Gazagnes |
| 2013/0117936 | A1 | 5/2013 | Stryker |
| 2015/0066117 | A1* | 3/2015 | Koch ................. A61G 11/002 607/100 |
| 2019/0000703 | A1* | 1/2019 | Underwood ............. G01K 3/14 |

FOREIGN PATENT DOCUMENTS

| | | |
|---|---|---|
| JP | 3127019 | 10/2006 |
| WO | WO 1997-11663 | 4/1997 |
| WO | WO 2000-24348 | 5/2000 |
| WO | WO 2004-084781 | 10/2004 |
| WO | WO 2008-038198 | 4/2008 |
| WO | WO 2009-131853 | 10/2009 |
| WO | WO 2011-022525 | 2/2011 |
| WO | WO2012-161870 | 11/2012 |

OTHER PUBLICATIONS

"Phase Change Materials", Microtek Laboratories, [retrieved from the internet on Jul. 22, 2019], URL <http://microtekiabs.com/how-do-pcms-work.html>, pp. 1-3.

"Phase Change Materials", Textile World, [retrieved from the internet on Jul. 22, 2019], URL <www.textileworld.com/Issues/2004/March/Features/Phase_Change_Materials>, pp. 1-11.

"Phase-change material", Wikipedia, [retrieved from the internet on Jul. 22, 2019], URL <http://en.wikipedia.org/wiki/Phase-change_material>, pp. 1-26.

Mei, "Unidirectional Fabric Drape Testing Method", National Institutes of Health, 2015, URL <https://www.ncbi.nlm.nih.gov/pmc/articles/PMC4657933/>, pp. 1-15.

* cited by examiner

RADIATIVE WARMING SYSTEM

CROSS REFERENCE TO RELATED APPLICATIONS

This application claims priority from U.S. Provisional Application Ser. No. 62/681,735, filed Jun. 7, 2018, the disclosure of which is incorporated by reference in its entirety herein.

BACKGROUND

Warming a person during surgery affords clinical benefits, such as prevention or treatment of hypothermia, encouragement of immune system function, promotion of wound healing, reduction of infection rates, and mitigation of discomfort.

Patient warming devices such as conductive and convective warming devices can be useful in preventing anesthesia-related hypothermia in mammalian patients. While radiative patient warming devices have been particularly useful in warming infant patients, the principles have not been applied to adult patients during surgical procedures.

SUMMARY

While infant incubators have been used, these devices do not typically provide radiative heat from beneath the contact surface. Some solutions, such as that proposed by Khodak in US 2011/0046433, do provide light from beneath the contact surface but would not be useful with an adult patient due to the larger surface area of the adult patient.

Aspects of the present disclosure relate to a warming system. The warming system includes a light device having a light source configured to be positioned proximate to a patient support having a patient support surface. The light source can also be configured to generate infrared radiation. The warming system can also include a flexible sheet having a first side configured to reflect at least some of the generated infrared radiation from the light device toward a portion of the patient support surface.

While the above-identified figures set forth several embodiments of the disclosure other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION

Aspects of the present disclosure relate to an infrared (IR) heating system with a light device configured to direct IR radiation generated at or beneath a patient and an IR reflective sheet to reflect the IR radiation onto the patient. Further, by mounting the light source of the light device to below a plane of a patient support surface, the light device can be out of the way of clinicians and allow infrared heating for a patient during a surgical procedure.

Figure 1A:
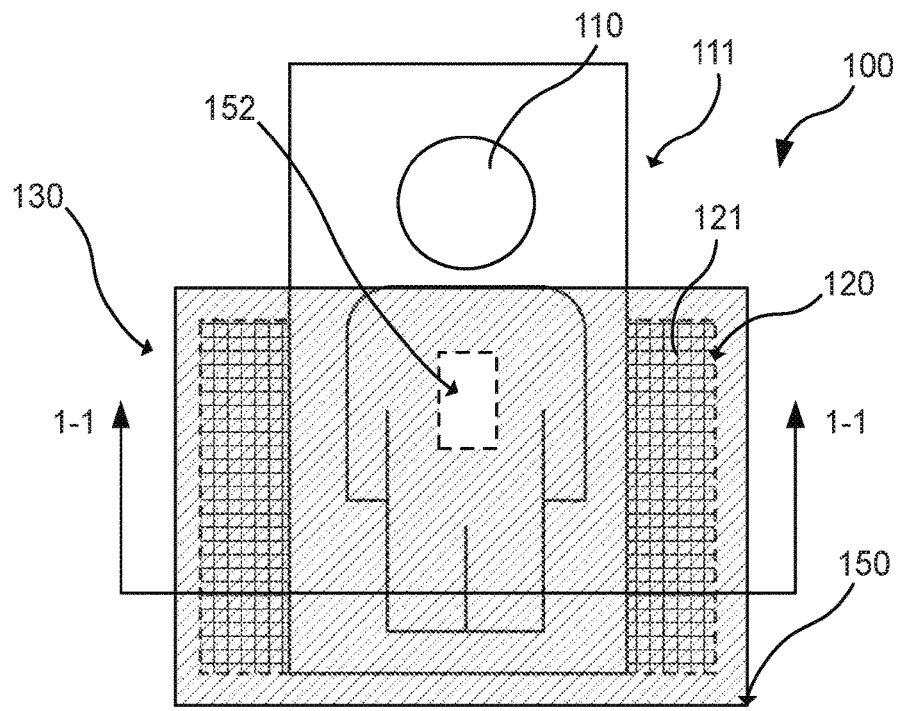
FIG. 1A illustrates an elevational view of a system of warming a patient using infrared radiation, according to various aspects of the present disclosure.
Figure 1B:
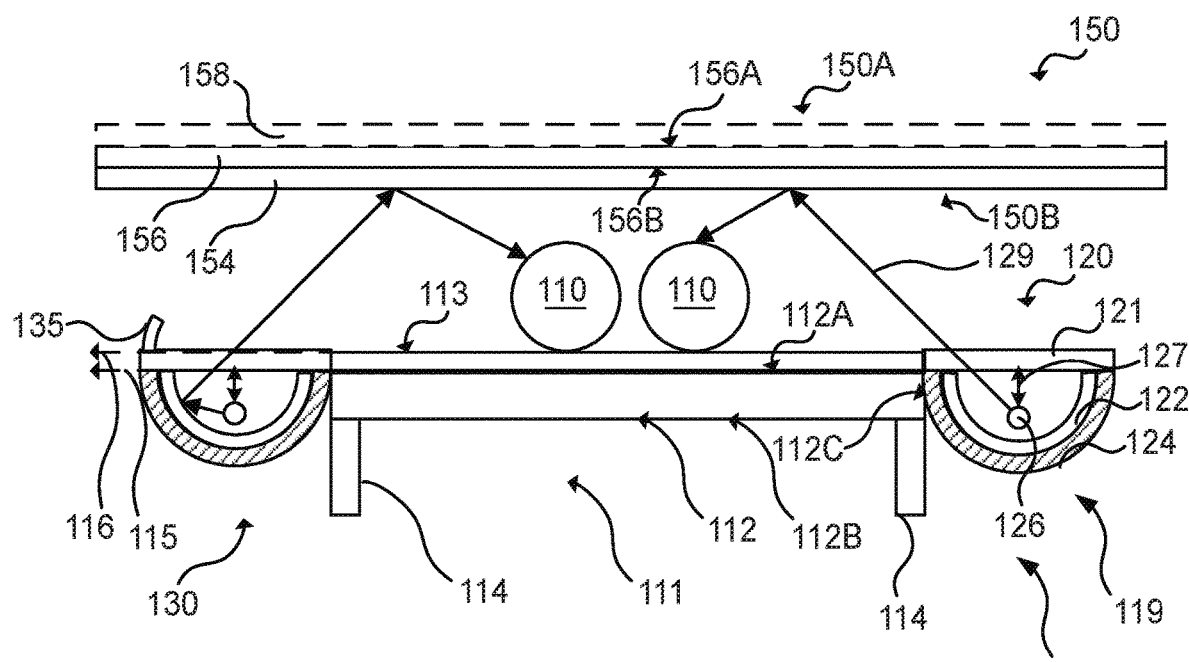
FIG. 1B illustrates a top-bottom cross sectional view of the system in FIG. 1A taken along lines 1-1, according to various aspects of the present disclosure.

FIGS. 1A-B illustrate a system 100 of infrared heating, according to various embodiments. The system 100 can generate IR radiation 129 and direct the IR radiation onto a patient 110. The patient 110 can be a surgical patient. In at least one embodiment, aspects of the present disclosure do not relate to infant warmers and are used in a surgical or pre-operative setting.

The patient 110 can be supported by a patient support 111. The patient support 111 can be movable or fixed. Movable patient supports can include beds, gurneys, stretchers, or other devices that are designed to be moved with a patient. Fixed patient supports 111 can include surgical tables or devices that are not designed to be mobile with a patient 110 supported by the patient support 111. In at least one embodiment, the patient support 111 can have a planar element that is substantially parallel to the ground.

The patient support 111 can have a patient support surface 112 which supports the weight of a patient 110 and distributes the weight over a larger surface area (which can be defined by a plane 116 of the patient support surface 112). The patient support surface 112 can have various surfaces such as a first major surface 112A, a second major surface 112B, and a third major surface 112C. The first major surface 112A can be facing the patient. In at least one embodiment, the first major surface can define a top plane 116 where a light source 126 of a light device 120 does not extend past the top plane 116. The second major surface 112B can be floor-facing. In at least one embodiment, the light source 126 of the light device 120 does not extend past the bottom plane 115. The third major surface 112C can be on the side of the patient support surface 112. In at least one embodiment, the light device 120 can be positioned proximate to the second major surface 112B and or the third major surface 112C.

In at least one embodiment, a patient contact surface 113 (e.g., a mat) can rest on top of the patient support surface 112. The patient contact surface 113 can provide comfort to the patient 110 and reduce pressure at pressure points. The patient contact surface 113 can be rigid, semi-rigid, or flexible. In at least one embodiment, the patient contact surface 113 can include air-bladders to lift the patient, reduce source, and/or provide comfort to the patient. In at least one embodiment, the patient contact surface 113 can have a side that is reflective (such as the side contacting 112A or on the patient-facing surface). In at least one embodiment, the patient contact surface 113 is an operating room pad. Any portion of the contact surface 113 can be configured to reflect IR radiation.

The patient contact surface 113 or the patient support surface 112 can be configured to allow passage of selected wavelengths of electromagnetic radiation, in particular, wavelengths from 700 nm to 1 mm (i.e., near IR and IR). In at least one embodiment, the patient contact surface 113 can also be configured to absorb IR radiation to heat the patient contacting side of the patient contact surface 113. In at least one embodiment, a portion of the patient contact surface 113 or the patient support surface 112 can be transparent. As used herein, transparent can refer to a physical property of allowing light to pass through the material without being scattered or can also refer to translucent (i.e., it allows light to pass through, but does not necessarily follow Snell's law; the photons can be scattered at either of the two interfaces where there is a change in index of refraction, or internally). By allowing light to pass through the material of patient contact surface 113, the patient 110 can be warmed from underneath the patient support 111 as well as from above (i.e., via reflected light). In at least one embodiment, the patient contact surface 113 can be a conductive heater designed to heat in response to an electrical current or warmed fluid.

Figure 2:
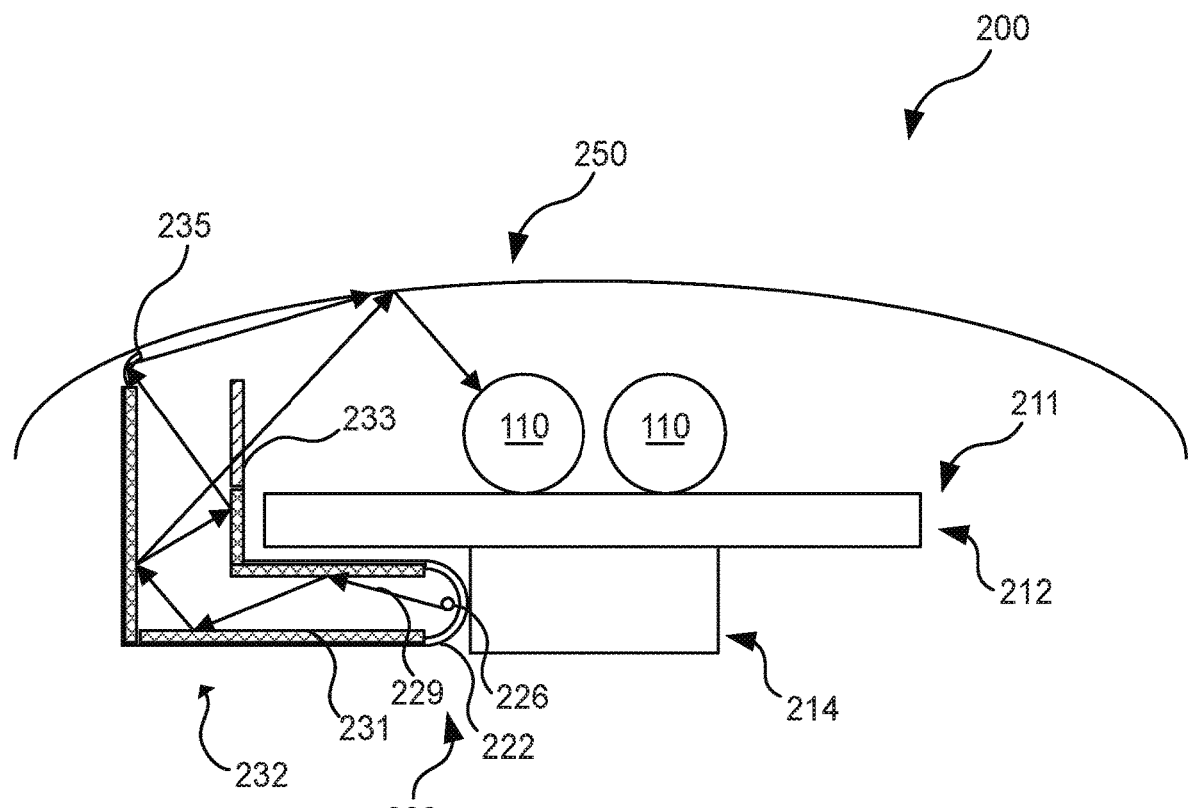
FIG. 2 illustrates a top-bottom cross sectional view of a system, according to various aspects of the present disclosure.

The patient support 111 can also have one or more load-bearing support members 114. Although a plurality of support members 114 are shown in FIG. 1B, there can also be a single support member 114 (e.g., as shown in FIG. 2). The support members 114 can support the patient support surface 112 and the patient 110 by bearing weight. In at least one embodiment, the light devices 120, 130 can also be contacting at least one patient support member 114.

The system can include one or more light devices (e.g., 120, and 130). The light device 120 is shown in more detail in FIG. 1B. The light device 120 can generate IR radiation that can be applied to the patient 110. As used herein, the term IR radiation refers to electromagnetic radiation with longer wavelengths than those of visible light. IR wavelengths can extend from 700 nm to 1 mm and includes near-IR wavelengths.

The light device 120 can include a light source 126. The light source is responsive to an electrical current which causes the light source to emit IR radiation. While other wavelengths of light can be generated by the light source 126, in at least one embodiment, a majority of the light produced (measured by intensity) is IR radiation. In at least one embodiment, the light source 126 can be defined by a power density. The power density of the light source 126 can be at least 0.5 watts per square millimeter. Examples of the light source 126 can include halogen, incandescent bulbs or light emitting diodes. The light source 126 can also be at least 200 W overall (e.g., multiple 50 W bulbs). Although light source 126 is shown as a single element, the light source 126 can also include a plurality of light elements sufficient to generate IR radiation for heating a patient. Each light element can also be separately controllable. For example, a first light element can be activated while a second light element is not activated to reduce the overall intensity of the IR radiation. Thus, the patient can be warmed in zones with each zone being exposed to different levels of IR radiation. The light source 126 can also be attached to a portion of the housing of the light device.

The light device 120 can also include a cover 119. The cover 119 includes one or more cover elements such as cover element 121 and cover element 122.

Cover element 121 can protect a patient 110 or clinician by preventing the patient 110 or clinician from touching the light source 126. The cover element 121 can also be configured to allow at least some of the IR radiation to pass through. For example, the cover element 121 can block no greater than 50%, no greater than 40%, no greater than 30%, no greater than 20%, or no greater than 10% of the IR radiation from the light source 126. The cover element 121 can have a plurality of openings formed therein. For example, the cover element 121 can be a sheet of material (such as a metal) with openings formed therein to allow the light to pass. In at least one embodiment, the cover element 121 does not absorb a significant amount of heat from the light source 126. As shown, the cover element 121 is shown as a grill or a grating (i.e., any regularly spaced collection of essentially identical, parallel, elongated elements) configured to prevent hands from touching the light source 126. The cover element 121 can also be solid such as a sheet of transparent material (e.g., glass, polymer, aerogel).

In at least one embodiment, the light source 126 can be a standoff distance 127 from the surface 112A or the cover element 121. For example, the light source 126 can have an air gap with the cover element 121. The standoff distance 127 can be a distance that is a lower intensity to prevent burning a patient's 110 skin. For example, the standoff distance can be at least 2 cm, at least 3 cm, at least 4 cm, or at least 5 cm.

The cover 119 also includes a cover element 122. The cover element 122 can obstruct at least some of the IR radiation 129 from the light source 126. The cover element 122 can further have at least one reflective surface. For example, cover element 122 can have an interior surface facing the light device and the interior surface is reflective. The cover element 122 can be made from metal, polymer, metallicized polymers, or other reflective materials. The cover element 122 can be arranged to direct the IR radiation 129 from the light source 126 toward the major surface 112A or patient 110. For example, the cover element 122 is shown obstructing IR radiation 129 directed toward the bottom direction of the patient support 111 and directing the IR radiation 129 upwards. Although various configurations are possible (such as using a plurality of flat reflectors arranged in a trapezoidal shape), the cover element 122 is shown as parabolic in shape.

In at least one embodiment, a portion of the cover element 122 can be proximate to (e.g., above, at, or below) the top plane 116 formed by the patient support surface 112A. For example, a portion of the cover element 122 is planar with the top surface 112A. Specifically, at least one of the edges of the first cover element are planar with the top surface 112A.

In at least one embodiment, the light device 120 can have an optional reflector 135 disposed above the plane 116 of the top surface 112A. The reflector 135 can be a separate element and attached to the light device 120. The reflector 135 can be configured to further direct IR radiation 129 to the patient. The reflector 135 can be configured to allow IR radiation 129 from the light device to reach a top side 112A of the patient support surface 112. In at least one embodiment, the light device 120 can have an insulating layer 124 (e.g., formed from a silica aerogel, fiberglass, nonwoven polymers, or air) disposed on a portion of the light device 119. For example, the insulating layer 124 can be disposed on the exterior surface of the cover element 122.

The light device 120 can be configured to be disposed, attached, or mounted to any portion of the patient support 111. Preferably, the light device 120 is mounted proximate to the patient support surface 112A (e.g., a position such that the light source 126 is at or below a plane 116 of the patient support surface 112A). For example, the light source 126 can be positioned below the patient support surface 112A even though a portion of the light device 120 may be positioned above the patient support surface 112A. In at least one embodiment, the light device 120 is planar with the patient support surface 112A. The light device 120 can also be positioned adjacent to the patient support surface 112. The light device 120 can also be mounted to an arm board of the patient support 111.

In at least one embodiment, the light device 120 can be configured to be (releasably) attached to a patient support surface 112, a patient support member 114, or even the patient contact surface 113 if a majority of the surface area of the light device 120 is below the plane 116 of the surface 112A. For example, at least one of the light devices 120, 130 can be attached to the patient contact surface 113 which can lift the patient to a position above the patient support surface 112 and provide comfort to the patient 110. The light source 126 can be below the plane 116 of the top surface 112A or the plane established by the patient 110. In at least one embodiment, the majority of the surface area of a housing (not shown) of the light device 120 can be below the plane 116 of the surface 112A. In at least one embodiment, light devices 120, 130 can be connected to each other through the patient contact surface 113 and be releasably disposed on the surface 112A. For example, in this configuration, the patient contact surface 113 and the light devices 120 and 130 can be removed as a single unit and transported between different patient supports 111.

The system 100 also includes a flexible sheet 150. The flexible sheet 150 is configured to drape over the patient 110 and reflect IR radiation 129 toward the patient 110. The sheet 150 can also include a top side 150A and a bottom side 150B. The bottom side 150B can be the patient facing side and is configured to reflect some of the generated infrared radiation to a portion of the patient support surface 112 or the patient contact surface 113. The flexible sheet 150 can have a variety of configurations. For example, the flexible sheet 150 can include one or more layers.

In at least one embodiment, the flexible sheet 150 can have one or more holes formed from any layer of the flexible sheet 150 therein. Each hole can be removably covered with a reflective sheet such that the reflective sheet can be removed so that the light from the light source is not reflected. Doing so can advantageously "vent" the light at the hole.

In at least one embodiment, the system 100 can also include a rigid sheet (not shown).

Layer 156 can be a structural layer and provide drapability characteristics useful in a medical drape. The layer 156 can be formed from a flexible material such as a (continuous) polymer sheet, woven, or nonwoven material. For example, a nonwoven drape can be useful in surgical procedures. In at least one embodiment, the polymer can be a polyester film such as polyethylene terpthalate.

The layer 156 is preferably opaque but can also be transparent. In at least one embodiment, the flexible sheet 150 can be entirely transparent. For example, the layer 158 or layer 156 can be coated with blue light absorber which absorbs at least wavelengths of light from 450 to 495 nm. An example of a blue light absorber can be similar to that found under the trade designation Skylet from Carl Zeiss (Germany). The result of a transparent sheet 150 can be IR reflectance to reduce a patient's radiation heat loss and at the same time are absorptive for waste energy from energy-saving high intensity lamps which can turn blue light peaks into heat.

The layer 156 can have drapability characteristics. For example, drape is the way that a material hangs under its own weight. In at least one embodiment, the layer 156 can have a drape coefficient no greater than 0.7, no greater than 0.50, or no greater than 0.3. The drape coefficient can describe a ratio of projected pleating fold area formed by a piece of fabric after draping under its own weight to the original area of this piece of fabric without draping. Drape can be defined by the Cusick Drape test which can be described in greater detail by Mei at https://www.ncbi.nlm.nih.gov/pmc/articles/PMC4657933/. The layer 156 can also have enough strength to support one or more sensors.

Layer 156 can have a side 156A and an opposing side 156B. The side 156B faces towards the patient 110 or patient support surface 112. The side 156B can have a layer 154 of material that is reflective. For example, an IR reflective material can be part of a metalized layer 154 such as aluminum or steel. The metalized layer 154 can include metalizing on one or core portions of the side 156B. In at least one embodiment, the layer 154 and/or 158 can also include a thermally sensitive pigment coating. The thermally-sensitive pigment coating can be configured to change reflective properties based on a temperature. For example, the temperature can correspond to a body temperature of the patient 110 and be configured to change from a light color (e.g., white) to a dark color (e.g., black) when the temperature is between 37 and 43 degrees Celsius. Thus, the thermally-sensitive pigment will reflect light to the patient 110 at the temperature but stop reflecting light to the patient 110 when pigment is getting too hot.

The sheet 150 can also have an optional layer 158 of material disposed on side 156A. The layer 158 can provide insulative properties (to prevent heat from escaping) or additional heating properties. For example, the layer 158 can include a thermally absorptive coating. The thermally absorptive coating can be configured to absorb infrared light 129 from the light device 120 or from an additional elevated light device. For example, the thermally absorptive coating can also absorb IR radiation from the environment or an external heat lamp to aid in patient heating for local warming.

In at least one embodiment, the layer 158 can also include a phase change material. A phase change material is a material that stores and releases large amounts of energy in the form of heat during the transition from one state of matter to another state of matter. Phase change materials can be organic, inorganic, or eutectic. Examples of organic phase change materials include paraffins or oils. Multiple phase change materials with multiple setpoints can also create a gradient within a layer 158 because the outer side 150B needs to be at a higher temperature than the inner side 150A to be effective. The phase change materials can preserve the body temperature of a patient at a level of around 37° C.

In at least one embodiment, the sheet 150 can also include a region 152. The region 152 can be present in at least one layer. For example, each layer of sheet 150 can have a region 152 that is aligned with the other layers. The region 152 can include a second material that is different from the material that forms any of the layers. The second material can include a conformable incise drape (that is minimally reflective). For example, the incise drape can be transparent and/or have antimicrobial properties. Examples of incise drapes are commercially under the trade designation Ioban or Steri-drape from 3M (Saint Paul, Minn.).

FIG. 2 illustrates a system 200 that includes a light device 220 that is disposed underneath a patient support surface 212 proximate to a patient support 211. IR radiation 229 is directed toward the patient 110 by a light guide 232.

The system 200 includes a flexible sheet 250, the flexible sheet 250 can be constructed similar to the flexible sheet 150 described in FIG. 1.

The system 200 includes a patient support 211 which includes the patient support surface 212 and the patient support member 214. The patient support 211 is configured similar to the patient support 111 described in FIG. 1.

The system also includes a light device 220 which is configured similar to the light device 120 described in FIG. 1. The light device 220 includes a light source 226 which generates IR radiation 229 and includes a cover element 222 that is shown as being parabolic in shape. The light device 220 is mechanically coupled to a light guide 232 such that the IR radiation 229 is transmitted from a remote location (e.g., non-proximate to the patient 110) to the top surface of the patient support surface 212.

For example, the light guide 232 can be configured to direct light from a light device 220 mounted under the patient support surface 212. For example, the light device 220 can be mounted to a pole, on the floor, or on a bottom side of the patient support surface 212 or the support member 214. The light guide 232 is shown as a pipe with walls. The walls of the pipe can be formed from a sheet of material. The pipe can be tube-shaped and have an interior surface and a first opening and a second opening formed therein. In at least one embodiment, the first opening is coupled to the light device 220, and at least part of the IR radiation 229 is reflected by the interior surface of the pipe.

The walls can be formed from a material that is reflective (such as a metal) and/or a reflective material 231 is disposed on at least a portion of the interior surface of the wall. For example, the reflective material can include a multi-layer reflective film disposed on the interior surface.

A portion of the light guide 232 can also include a light permissive portion 233. For example, the light permissive portion 233 can be transparent and allows light through but prevents patient 110 from reaching into the interior surface of the light guide 232. The light permissive portion 233 can be similar to the cover element 121 in FIG. 1.

The light guide 232 can also have a coverlet 235 disposed thereon. The coverlet 235 can be configured to direct IR radiation 229 onto a portion of the patient support surface 212.

In at least one embodiment, the light guide 232 is flexible and can be liquid-filled. For example, a heat enhancing liquid can be used to transmit some heat energy to the patient support surface 212. The light guide 232 can also be formed from glass such as a plurality of glass fibers sufficient to transmit IR radiation 229.

Figure 3:
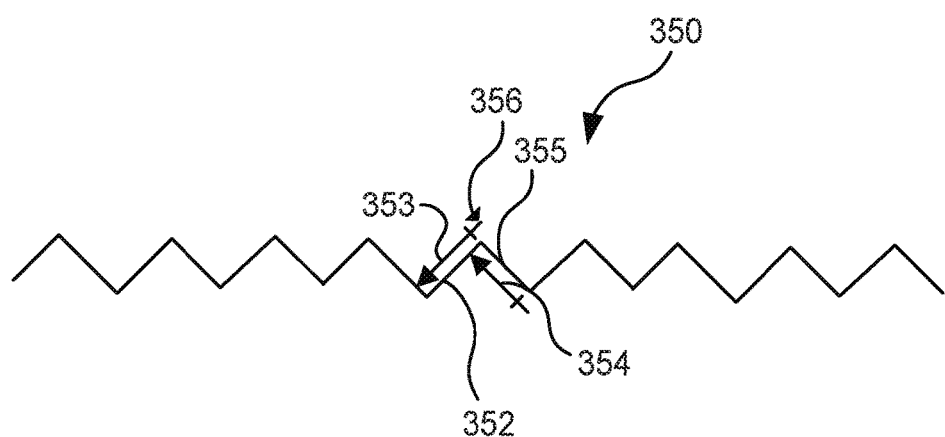
FIG. 3 illustrates a top-bottom cross sectional view of a pleated sheet, according to various aspects of the present disclosure.

FIG. 3 illustrates a sheet 350 that is an embodiment of flexible sheet 150 in FIG. 1 showing a pleated construction. The pleated construction can refer to pleats or asymmetric ridges. A pleated sheet 350 can unexpectedly increase an overall surface area of a three-dimensional patient that is exposed to IR radiation. The sheet 350 can include a set of pleat folds that form a plurality of flute peaks (e.g., peak 356). The pleats 352, 355 can have a pleat length 353, 354. Even though the pleats 352, 355 are shown as having the same length, the pleat lengths 353, 354 can have different lengths in an asymmetric configuration. Other shapes of pleats can also be formed such as sinusoidal pleats.

In at least one embodiment, the pleats can be oriented in a longitudinal direction relative to a patient. For example, a spine formed by a flute peak of the pleats can be oriented along sagittal plane the patient.

Figure 4:
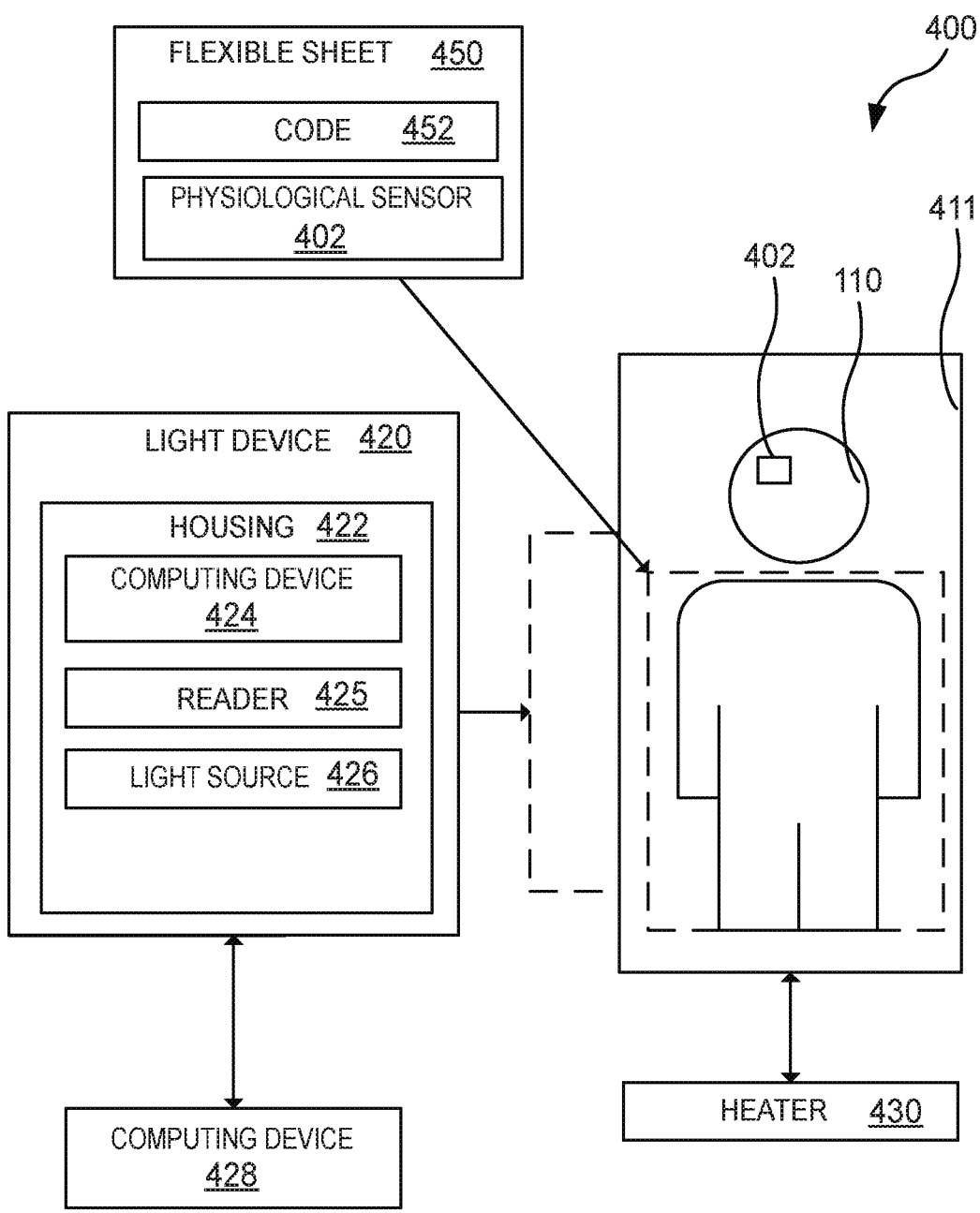
FIG. 4 illustrates a block diagram of a system of warming a patient using infrared radiation, according to various aspects of the present disclosure.

FIG. 4 illustrates a system 400 that includes one or more computing devices to control the operation of a light device.

The system 400 includes a patient 110. The patient 110 can be supported by the patient support 411 which is embodied by either patient support 111 or 211 described herein.

The system 400 can also include a heater 430 that is thermally coupled to the patient 110 and is configured to provide additional heating to the patient 110. For example, the heater 430 can be a convective or conductive heater proximate to the patient support 411. The heater 430 can augment the heating from the light device 420.

The system 400 can also include one or more sensors 402 that measure the patient 110 and are communicatively coupled to the one or more computing devices. In at least one embodiment, the sensor 402 can be a physiological sensor that measures one or more physiological properties of the patient 110. For example, the sensor 402 can measure the heart rate, the perspiration, the core temperature, the skin temperature, pulse oximetry, or combinations thereof. The sensor 402 can be disposed on the patient or proximate to the patient 110. For example, if the sensor 402 is an IR Camera, then the IR camera should be positioned such that the patient 110 is in the frame.

In at least one embodiment, the sensor 402 is a temperature sensor. The temperature sensor can be a core temperature sensor that measures a core body temperature of the patient 110. The sensor 402 can also measure a skin temperature sensor or a radiometer that measures exposure to the IR radiation.

The system 400 can also include a reflective flexible sheet 450 which is similar in construction to flexible sheets 150 or 350 described herein. The flexible sheet 450 can also include an optional code 452. The code 452 can be disposed on the flexible sheet 450 or formed integrally with one of the layers of the sheet 450. The code 452 is sufficient to identify the sheet 450. The code 452 is readable by the reader 425 described herein. The code 452 can be a QR code, bar code, plain text indication, or other indication. The code 452 may be used to indicate an authentic sheet 450. For example, the code 452 can be nonsensical if read on its own but a unique alphanumeric sequence can indicate a model or lot number of the sheet 450.

The sheet 450 can also have one or more sensors 402 disposed thereon. The sensors 402 are described herein. For example, an IR sensor can be disposed on the sheet 450 to measure exposure to IR radiation. A temperature sensor can also be disposed on a patient-facing surface of the sheet 450 to measure skin temperature of the patient 110. In at least one embodiment, the temperature sensor can be placed proximate to the light source and measure reflected or incident IR radiation generated by the patient.

The system 400 can also include a light device 420 which is exemplified by light device 120 described herein.

The light device 420 can also include a housing 422 that houses the components of the light device 420.

The light device 420 can include a reader 425 disposed proximate the housing 422 and communicatively coupled to the computing device 424. The reader can be an optical reader. For example, the reader 425 can be configured to read a code 452 or another characteristic of the sheet 450. For example, the reader 425 can measure a unique material characteristic such as reflectivity. For example, a reader 425 can read a reflectivity of the flexible sheet 450 to determine if the reflectivity is sufficient to use the sheet 450 in the system 400. In at least one embodiment, the reader 425 can also be used to analyze whether the code 452 is present and provide an indication of the code to the computing device 424.

The light device 420 can be communicatively coupled to a computing device 424. In at least one embodiment, the computing device 424 can be positioned in the housing 422. The computing device 424 can have one or more processors coupled to a memory, the memory has computing instructions as described herein. The computing device 424 can control the intensity of the IR radiation generated by the light source 426. In at least one embodiment, the computing device 424 can receive data corresponding to the code 452 from the reader 425, determine one or more characteristics regarding the flexible sheet 450, and perform at least one operation based on the one or more characteristics.

The computing device 424 can be configured to control light source based on a characteristic of the sheet 450. The computing device 424 can prevent a light source 426 from generating light if the code 452 or other characteristic is not present. For example, if the sheet 450 is not sufficiently reflective, then the computing device 424 can prevent the light source 426 from activating. In another example, the computing device 424 can be configured to prevent the light source 426 from activating based on whether the sheet 450 is authentic.

In at least one embodiment, after receiving the code from the reader 425, the computing device 424 can determine that the code 452 indicates a model number of the sheet 450 whereby the reflectivity and surface area of the sheet 450 can be further determined. For example, if the sheet 450 has a first reflectance that is less than a base reflectance, then a higher intensity of IR radiation can be generated by the light source 426 as compared with the base reflectance.

In at least one embodiment, the computing device 424 can communicate with a computing device 428 to verify the code 452 or obtain additional information relating to the code 452. For example, the code 452 can be sent to a remote computing device 428 which returns a characteristic (such as product authenticity or sheet features) to the computing device 424.

The computing device 424 can also be communicatively coupled to the sensor 402 to form a closed-loop feedback control. The computing device 424 can be configured to be responsive to the sensor 402. For example, the computing device 424 can receive a core or skin temperature of patient. The computing device 424 can be configured to read a temperature from the temperature sensor, determine whether a threshold is met by the temperature, and perform at least one operation based on the temperature. Multiple temperature sensors can be used to control the output of at least some of the light sources such that specific zones of heating can be independently operated.

Figure 5:
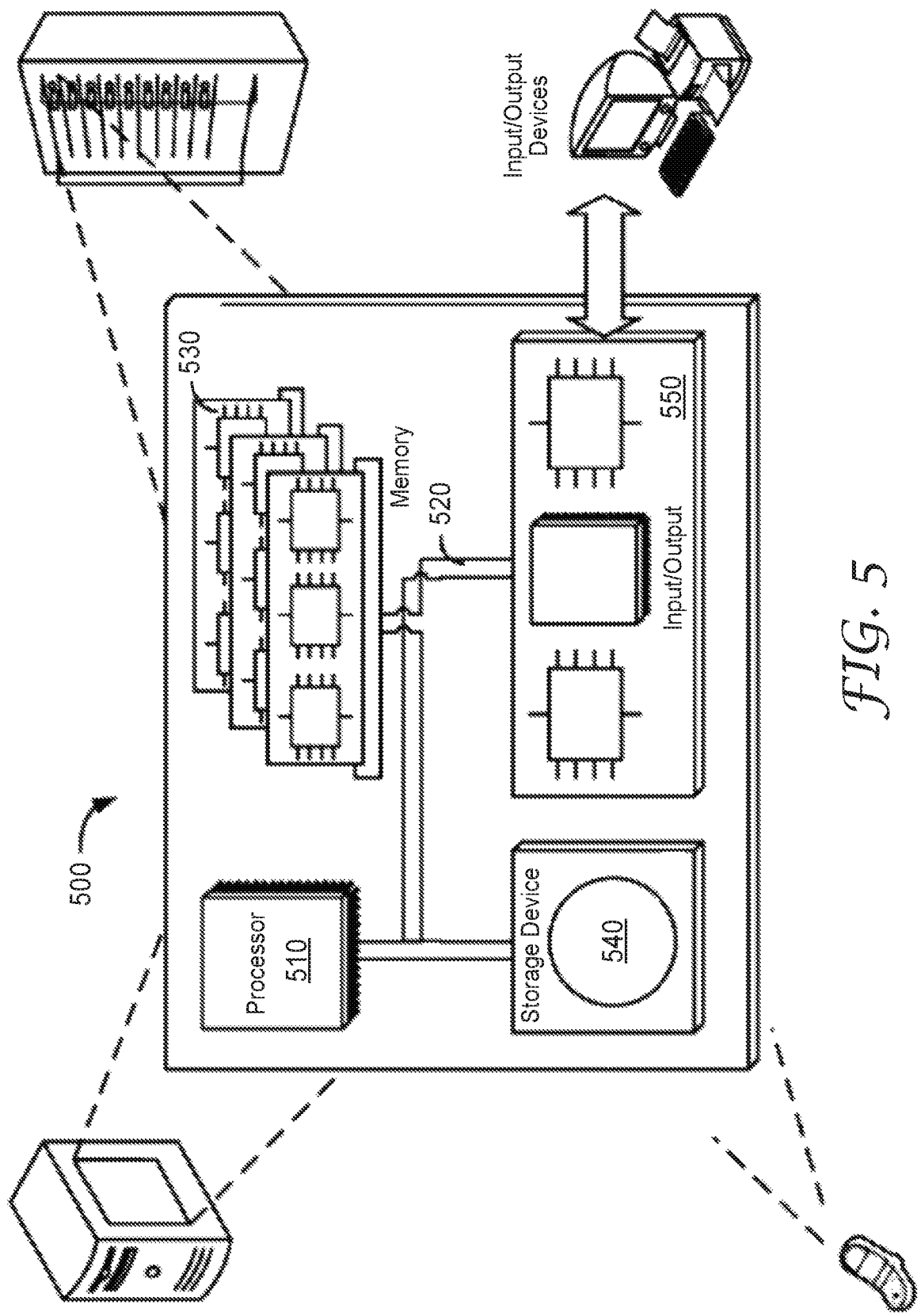
FIG. 5 illustrates a block diagram of a computing device, according to various aspects of the present disclosure.

FIG. 5 shows a detailed example of various devices that may be configured to execute program code to practice some examples in accordance with the current disclosure. For example, computing device 500 may be a computing device that performs any of the techniques described herein. In the example illustrated in FIG. 5, a computing device 500 includes a processor 510 that is operable to execute program instructions or software, causing the computer to perform various methods or tasks. Processor 510 is coupled via bus 520 to a memory 530, which is used to store information such as program instructions and other data while the computer is in operation. A storage device 540, such as a hard disk drive, nonvolatile memory, or other non-transient storage device stores information such as program instructions, data files of the multidimensional data and the reduced data set, and other information. The computer also includes various input-output elements 550, including parallel or serial ports, USB, Firewire or IEEE 1394, Ethernet, and other such ports to connect the computer to external device such as a printer, video camera, surveillance equipment or the like. Other input-output elements may include wireless communication interfaces such as Bluetooth, Wi-Fi, and cellular data networks.

Figure 6:
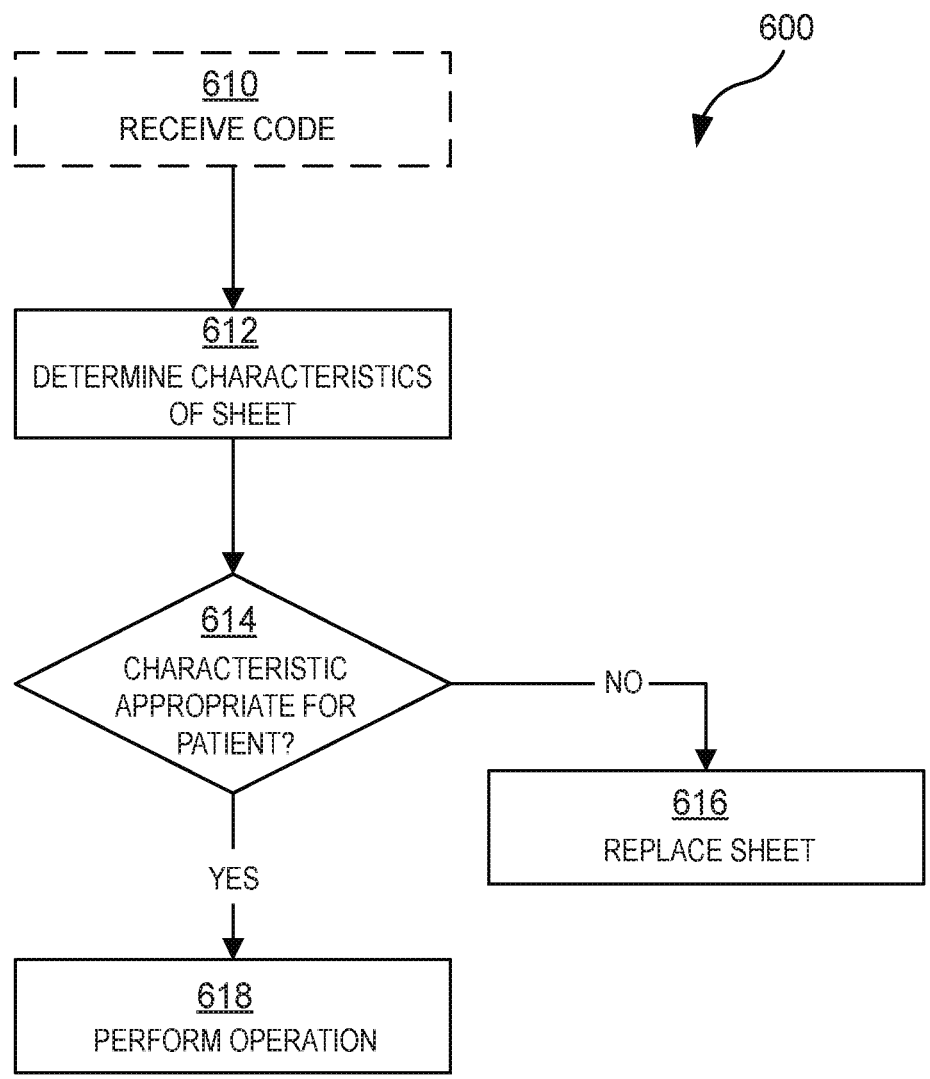
FIG. 6 illustrates a flowchart of a method of performing an operation based on characteristics of a sheet, according to various aspects of the present disclosure.

FIG. 6 illustrates a flow chart of a method 600 for determining characteristics of the sheet. The method 600 can begin at block 610.

In block 610, the computing device can optionally receive a code from a reader. As discussed herein, the code can indicate an alphanumeric sequence or a pattern that is recognizable to the computing device to associate the code with information. For example, the code can indicate a model number or that the product is authentic. The reader can read the code and transmit information relating to the code to the computing device.

In block 612, the computing device can determine characteristics of the sheet. For example, the code from block 610 can reveal many characteristics of the sheet, e.g., the model number of the sheet, lot number, date of manufacture, physical properties of the sheet such as reflectivity, or opaqueness, product authenticity, or combinations thereof. The characteristics of the sheet can also be determined by the reader itself. For example, the reader can be configured to measure the reflectivity of the sheet by applying a light (potentially an IR radiation from the light source) and measuring the amount of reflected light.

In block 614, the computing device can determine whether the characteristic is appropriate for the patient or the system. The computing device can also receive details regarding physiological properties of the patient that can affect the absorption of IR radiation or type of procedure. For example, the computing device can receive information regarding the height, weight, age of the patient from a remote computing device. In at least one embodiment, the computing device can determine whether the characteristic is appropriate for the patient based on at least one physiological property of the patient. For example, a patient with a high body mass index would not likely use a sheet size that is below a certain size. If the physiological properties of the patient indicate that the patient has higher heating requirements, the sheet can be appropriate when the sheet has an insulating layer disposed thereon.

Further, the computing device can also receive information regarding the procedure for the patient. For example, the computing device can receive information that the patient is having a knee surgery and determine that the only appropriate drapes are those that are knee drapes, then the computing device can determine whether the knee drape is present based on the code.

The computing device can determine whether the characteristic is appropriate based on whether the characteristic satisfies a condition. The condition can also be predetermined by the clinician. For example, if the characteristic is sheet manufacture date, and the condition is an expiration date, then the condition is satisfied when the sheet manufacture date is less than the expiration date. Other conditions can include whether the sheet is being recalled.

In block 616, the computing device can instruct the clinician to replace the sheet. For example, if the sheet is not appropriate for the patient or the system, then the sheet can be replaced by the clinician. The computing device can indicate that the light source is not activated and request that the clinician use another sheet.

In block 618, the computing device can perform one or more operations in response to the characteristic being appropriate for the patient or system. In at least one embodiment, the operation can include activating one or more elements of the light source. For example, if the sheet has a low level of reflectance, then the computing device can increase the intensity of the light source. In at least one embodiment, the operation can also include displaying an alert for a clinician that the sheet is appropriate.

Figure 7:
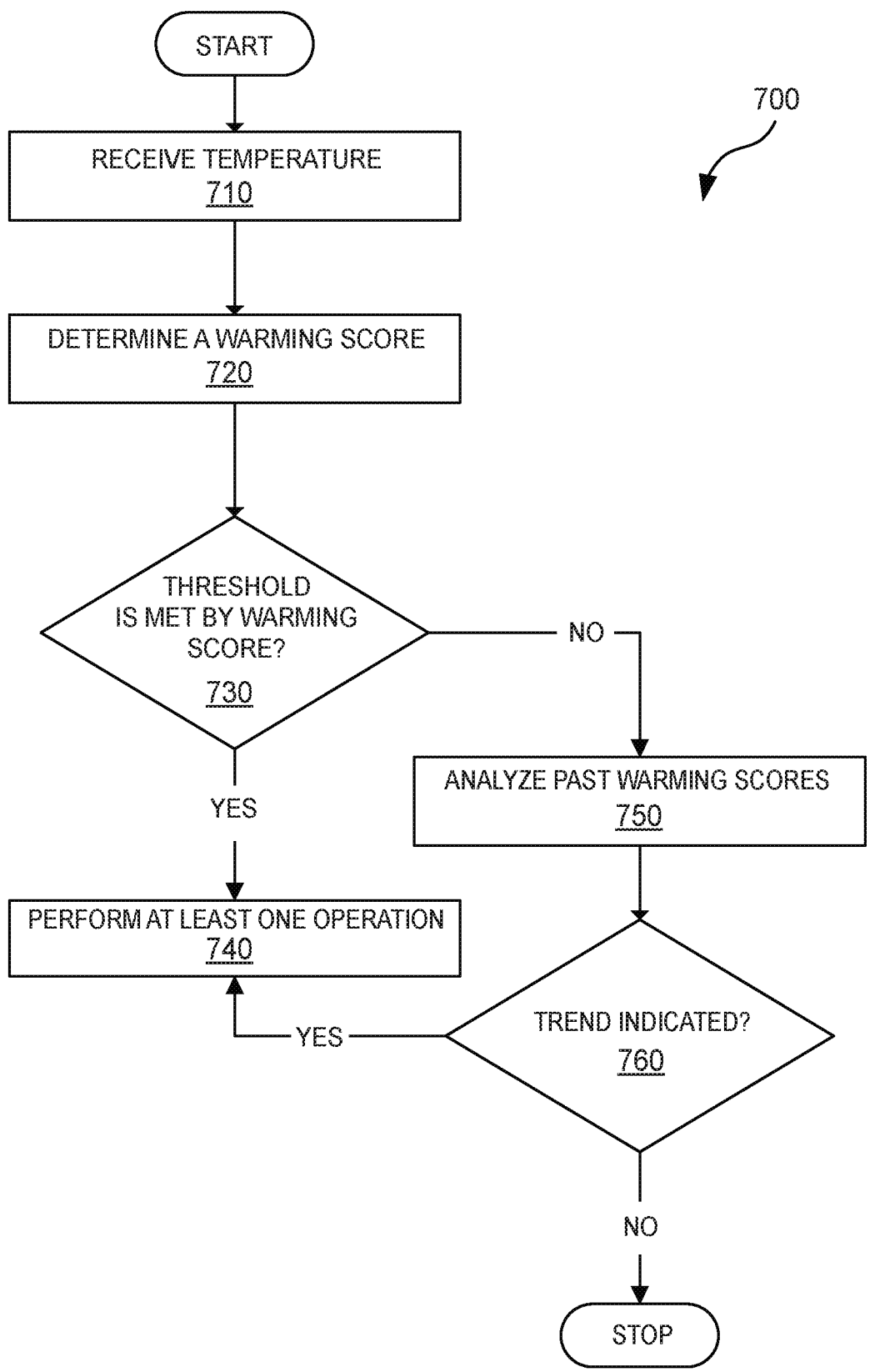
FIG. 7 illustrates a flowchart of a method of performing an operation based on feedback from a temperature sensor, according to various aspects of the present disclosure.

FIG. 7 illustrates a flowchart of a method 700 for analyzing the skin temperature and core temperature of a patient. The method 700 can begin at block 710.

In block 710, the computing device can receive a temperature (e.g., a core temperature and the skin temperature) from the sensor. The sensors can measure one or both the skin temperature and the core temperature of a patient. The signals from the sensors can be received by the control mechanization (e.g., electrically or via radio frequency) and processed.

In block 720, the computing device can determine a warming score. The warming score can be indicative of the adequacy of warming for the patient. As the patient absorbs energy from the IR radiation, the body temperature of the patient may increase. If the core temperature of the patient increases past a threshold, vasodilation or even sweating may occur which can rapidly cool the patient and potentially negate any warming benefits. In at least one embodiment, the warming score can indicate the likelihood of the patient to undergo vasodilation. In another embodiment, the computing device can receive an indication of a patient condition to determine the warming score. For example, if a patient is diabetic, then the feet of the patient can be not warmed or have a relatively higher warming score. Although various metrics can be used, the warming score can be based on the relationship between the core temperature and the skin temperature. In at least one embodiment, the warming score can be based on a difference between the core temperature and the skin temperature of the patient.

In block 730, the computing device can determine whether a warming score meets a threshold. The threshold can be based on adequate warming or inadequate warming. If the threshold is based on a difference between core temperature and skin temperature, a difference of no greater than +/−0.1, 0.2, 0.3, 0.4, 0.5, 0.6, 0.7, 0.8, 0.9, 1, 2, 3, 4, or 5 degrees Celsius can indicate adequate warming (meaning that the threshold is met). In at least one embodiment, if the skin temperature of the patient is substantially at or above the core temperature, then it may be indicative of adequate pre-warming of the patient.

In block 740, the computing device can perform at least one operation based on the warming score meeting the threshold. For example, the operation can include interacting with the controller to change the first heat setting to the second heat setting. The heat setting can include a temperature level, a fan speed, or combinations thereof. In at least one embodiment, the first heat setting can be higher than the second heat setting. For example, in response to a warming score indicating that the patient is warmed, the computing device can instruct the warming device to reduce the energy transfer to the patient. Alternatively, the computing device can also instruct the warming device to increase energy transfer to the patient.

In at least one embodiment, the operation can also be changing any display settings of the computing device. For example, a color of a font for the temperature. The operation can also trigger a prediction of total time left in a pre-warming cycle of the warming device. For example, the prediction can be based on a rate of change between the core and skin temperatures and the heat applied by the warming device.

In at least one embodiment, the computing device can control the light source to warm sections of the patient. For example, the arms, legs, torso can be warmed separately depending on the surgical procedure. The computing device can also initiate a warming sequence based on a timed control (where the operation is activating the light source for a duration of time). The timed control can also use the readings from the sensors and the warming score.

In block 750, the computing device can analyze prior warming scores determine whether prior warming scores indicate a trend of increasing or decreasing values. In at least one embodiment, the trend is a rising difference between consecutive scores determined in block 720. For example, the temperature difference can appear to be decreasing over successive readings of temperature differences of the patient. In at least one embodiment, the trend can be based on point-to-point values of successive readings. Various statistical techniques can be used to account for spikes of scores off-trend such as rolling averages, or area under the curve. For example, if the overall trend is increasing but a point-to-point value shows decreasing, then rolling averages can remove the trend.

In block 760, the computing device can determine if a trend is indicated and, if so, perform at least one operation based on the trend in block 740.

Various examples and implementations will be described in detail. These examples should not be construed as limiting the scope of the present disclosure in any manner, and changes and modifications may be made without departing from the spirit and scope of the disclosure. Further, only some end uses have been discussed herein, but end uses not specifically described herein are included within the scope of the present disclosure. As such, the scope of the present disclosure should be determined only by the claims.

List of Illustrative Embodiments

1. A warming system, comprising:
 a light device having a light source, the light device configured to be positioned proximate to a patient support having a patient support surface, and configured to generate infrared radiation;
 a flexible sheet having a first side configured to reflect some of the generated infrared radiation from the light device toward a portion of the patient support surface.
1a. The warming system of embodiment 1, wherein the light source is configured to be positioned at or below a plane of the patient support surface.
2. The warming system of embodiment 1, wherein the light device is configured to be positioned adjacent to the patient support surface.
2a. The warming system of embodiment 1, wherein the light device is configured to be positioned at or below a plane of the patient support surface corresponding to a patient-facing major surface.
2b. The warming system of embodiment 1, wherein the light device is configured to be positioned at or below a plane of the patient support surface corresponding to a floor-facing major surface.
2c. The warming system of any of embodiments 1 to 2b, further comprising a patient contact surface.
2d. The warming system of embodiment 2c, wherein the patient contact surface is configured to contact the patient support surface and is attached to the light device.
2e. The warming system of embodiment 2d, wherein the patient contact surface is configured to be removable from the patient support surface with the light device attached.

2f. The warming system of any of embodiments 1 to 2b, wherein the flexible sheet is configured to reflect generated infrared radiation toward the patient contact surface.

2g. The warming system of any of embodiments 1 to 2f, further comprising a patient.

2h. The warming system of any of embodiments 1 to 2g, wherein the patient is a human adult patient.

2i. The warming system of any of embodiments 1 to 2h, wherein the patient is supported by the patient contact surface.

3. The warming system of any of embodiments 1 to 2i, wherein the light device is configured to be releasably mounted to a portion of the patient support.

4. The warming system of any of embodiments 1 to 3, wherein the light device is configured to be releasably attached to the patient support.

5. The warming system of any of embodiments 1 to 4, wherein the light device is planar with the patient support surface.

6. The warming system of any of embodiments 1 to 5, further comprising a cover having a first cover element that obstructs a portion of the light device.

7. The warming system of embodiment 6, wherein the first cover element obstructs light oriented toward the bottom direction of the patient support.

8. The warming system of embodiment 7, wherein the first cover element is parabolic.

9. The warming system of embodiment 8, wherein the first cover element has an interior surface facing the light device and the interior surface is reflective.

10. The warming system of embodiment 9, wherein the first cover element comprises an insulating layer disposed on an exterior surface.

11. The warming system of embodiment 10, wherein a portion of the first cover element is planar with the top surface.

12. The warming system of embodiment 11, wherein the edges of the first cover element are planar with the top surface.

13. The warming system of any of embodiments 6 to 12, wherein the cover comprises a second cover element that allows at least a portion of the infrared radiation to pass.

14. The warming system of embodiment 13, wherein the second cover element has a plurality of openings formed therein.

15. The warming system of embodiment 13 or 14, wherein the second cover element is at a standoff distance from the light source.

16. The warming system of embodiment 15, wherein the standoff distance is a distance that prevents burning of a patient's skin.

17. The warming system of embodiment 16, wherein the standoff distance is at least 5 cm.

18. The warming system of any of embodiments 1 to 17, further comprising a non-planar reflector configured to allow radiation from the light device to reach a top side of the patient support surface.

19. The warming system of any of embodiments 1 to 18, further comprising a light guide configured to direct light from a light device mounted on a bottom side of the patient support surface.

20. The warming system of embodiment 19, wherein the light guide comprises pipes formed from a sheet of material having an interior surface and a first opening and a second opening formed therein, wherein the first opening is coupled to the light device, and at least part of the infrared radiation is reflected by the interior surface of the pipe.

21. The warming system of embodiment 20, wherein the interior surface is reflective.

22. The warming system of embodiment 21, wherein the pipe comprises a multi-layer reflective film disposed on the interior surface.

23. The warming system of embodiment 19 or 20, wherein the light guide is liquid-filled.

24. The warming system of embodiment 19, wherein the light guide comprises glass.

25. The warming system of any of embodiments 19 to 24, wherein the light guide comprises a coverlet configured to direct radiation onto a portion of the patient support surface.

25a. The warming system of any of embodiments 1 to 25, wherein the light guide comprises a filter to filter visible light.

26. The warming system of any of embodiments 1 to 17, further comprising a reader communicatively coupled to a computing device, wherein the flexible sheet comprises a code, the computing device configured to receive data corresponding to the code from the reader, determine one or more characteristics regarding the flexible sheet, and perform at least one operation based on the one or more characteristics.

27. The warming system of embodiment 26, wherein the characteristic is product authenticity.

28. The warming system of embodiment 26 or 27, wherein the operation is providing control settings on the light device.

29. The warming system of any of embodiments 26 to 28, wherein the reader is an optical reader and the code is readable to the optical reader.

30. The warming system of any of embodiments 1 to 17, wherein the flexible sheet has a second side opposite the first side.

31. The warming system of embodiment 30, wherein the second side has a thermally absorptive coating disposed thereon.

32. The warming system of embodiment 31, wherein the thermally absorptive coating is configured to absorb infrared light.

33. The warming system of any of embodiments 1 to 32, wherein the flexible sheet comprises a polyester film.

34. The warming system of embodiment 33, wherein the polyester film comprises polyethylene terpthalate.

35. The warming system of embodiment 34, wherein the flexible sheet comprises a metalized layer.

36. The warming system of embodiment 35, wherein the metalized layer comprises metalizing only on one or more portions of the first side.

37. The warming system of any of embodiments 1 to 36, wherein the flexible sheet comprises a nonwoven layer.

38. The warming system of embodiment 37, wherein the nonwoven layer is vapor coated with aluminum.

39. The warming system of any of embodiments 1 to 38, wherein the flexible sheet comprises a thermally sensitive pigment coating.

40. The warming system of embodiment 39, wherein the thermally-sensitive pigment coating is configured to change reflective properties at a temperature.

41. The warming system of embodiment 40, wherein temperature is between 37 and 43 degrees Celsius.

42. The warming system of any of embodiments 1 to 34, wherein the flexible sheet is transparent.

42a. The warming system of any of embodiments 1 to 42, wherein the flexible sheet comprises a blue-light absorber configured to absorb electromagnetic radiation from 450 to 495 nm.
43. The warming system of any of embodiments 1 to 42, wherein the flexible sheet is pleated.
44. The warming system of any of embodiments 1 to 43, wherein the flexible sheet comprises a set of pleat folds that form flute peaks.
45. The warming system of embodiment 44, wherein the pleat fold is asymmetric.
45a. The warming system of any of embodiments 43 to 45, wherein a spine that is formed from the flute peaks are oriented along a coronal plane of the patient.
45b. The warming system of any of embodiments 1 to 45a, wherein the flexible sheet is usable as a medical drape.
45c. The warming system of any of embodiments 1 to 45b, wherein the flexible sheet has holes disposed therein.
45d. The warming system of any of embodiments 1 to 45c, wherein the flexible sheet further comprises partially removable covers disposed over the holes.
45e. The warming system of any of embodiments 1 to 45d, wherein the flexible sheet comprises a phase change material that changes phase at approximately 37 degrees Celsius. 46. The warming system of any of embodiments 1 to 45, wherein the patient support surface allows the passage of selected wavelengths of radiation.
47. The warming system of any of embodiments 1 to 46, wherein the patient contact surface comprises air bladders.
48. The warming system of any of embodiments 1 to 46, further comprising a conductive heater proximate the patient support surface.
49. The warming system of any of embodiments 1 to 47, further comprising a temperature sensor.
50. The warming system of embodiment 49, wherein the temperature sensor is a core temperature sensor.
51. The warming system of embodiment 49, wherein the temperature sensor is a skin temperature sensor disposed on a portion of the flexible sheet.
52. The warming system of embodiment 49, wherein the temperature sensor is an IR camera positioned such that a patient is in frame.
53. The warming system of embodiment 49, wherein the temperature sensor is a radiometer.
54. The warming system of any of embodiments 49 to 53, wherein a computing device is configured to read a temperature from the temperature sensor, determine whether a threshold is met by the temperature, and perform at least one operation based on the temperature.
55. The warming system of embodiment 54, wherein the temperature is a core body temperature of a patient.
56. The warming system of any of embodiments 1 to 55, wherein the light device comprises:
a reader communicatively coupled to a computing device,
the computing device communicatively coupled to the reader comprising one or more computer processors and a memory comprising instructions that when executed by the one or more computer processors cause the one or more computer processors to:
determine one or more characteristics of the flexible sheet using the reader,
determine whether the flexible sheet is appropriate for the system based on the characteristics; and
perform at least one operation based on whether the flexible sheet is appropriate.

57. The warming system of embodiment 56, wherein at least one of the one or more characteristics includes reflectivity of the flexible sheet.
58. The warming system of any of embodiments 56 to 57, wherein whether the flexible sheet is appropriate is based on product authenticity of the flexible sheet.
59. The warming system of any of embodiments 56 to 58, wherein the flexible sheet comprises a code readable by the reader and is indicative of product authenticity.
60. The warming system of any of embodiments 56 to 59, wherein the at least one operation includes activating the light source.
61. The warming system of any of embodiments 1 to 60, further comprising:
a sensor that measures physiological properties of a patient;
a computing device communicatively coupled to the sensor and comprising one or more computer processors and a memory comprising instructions that when executed by the one or more computer processors cause the one or more computer processors to:
receive the physiological property from the sensor;
determine a warming score based on the physiological property, wherein the warming score is indicative of a core body temperature of a patient;
determine whether the warming score meets a threshold;
perform at least one operation based on the warming score meeting the threshold.
62. The system of embodiment 61, wherein, to perform at least one operation, the memory comprises instructions that when executed by the one or more computer processors cause the one or more computer processors to provide instructions to the light device to change from a first heat setting to the second heat setting.
63. The system of embodiment 61 or 62, wherein the first heat setting includes activating a first set of bulbs for the light source and the second heat setting includes activating a second set of bulbs fewer than the first set of bulbs.

What is claimed is:
1. A warming system, comprising:
a light device having a light source, the light device configured to be positioned proximate to a patient support having a patient support surface and configured to generate infrared radiation;
a flexible sheet having a first side configured to reflect some of the generated infrared radiation from the light device toward a portion of the patient support surface, and wherein the light device comprises a housing,
a reader disposed at least partially within the housing and communicatively coupled to a computing device, the computing device comprising one or more computer processors and a memory comprising instructions that when executed by the one or more computer processors cause the one or more computer processors to:
determine one or more characteristics of the flexible sheet using the reader,
determine whether the flexible sheet is appropriate for the system based on the characteristics; and
perform at least one operation based on whether the flexible sheet is appropriate.
2. The warming system of claim 1, wherein the light device is configured to be positioned adjacent to the patient support surface.
3. The warming system of claim 1, wherein the light source configured to be positioned at or below a plane of the patient support surface and the light device is configured to be positioned at or below a plane of the patient support surface corresponding to a patient-facing major surface.

4. The warming system of claim 1, further comprising a patient contact surface, wherein the patient contact surface is configured to contact the patient support surface and is attached to the light device.

5. The warming system of claim 4, wherein the patient contact surface is configured to be removable from the patient support surface with the light device attached.

6. The warming system of claim 1, wherein the flexible sheet has a second side opposite a first side, wherein the second side has a thermally absorptive coating disposed thereon, wherein the thermally absorptive coating is configured to absorb infrared radiation.

7. The warming system of claim 1, wherein the flexible sheet comprises a polyester film or a nonwoven and a metalized layer disposed on the first side.

8. The warming system of claim 1, wherein the flexible sheet comprises a thermally sensitive pigment coating configured to change between a light color and a dark color at a temperature between 37 and 43 degrees Celsius.

9. The warming system of claim 1, wherein the flexible sheet is pleated over at least a portion thereof.

10. The warming system of claim 1, wherein the flexible sheet comprises a set of pleat folds that form flute peaks.

11. The warming system of claim 1, wherein the pleat fold is asymmetric.

12. The warming system of claim 1, further comprising a light guide configured to direct light from a light device mounted on a bottom side of the patient support surface.

13. The warming system of claim 1, wherein at least one of the one or more characteristics includes reflectivity of the flexible sheet.

14. The warming system of claim 1, wherein whether the flexible sheet is appropriate is based on product authenticity of the flexible sheet.

15. The warming system of claim 14, wherein the flexible sheet comprises a code readable by the reader and is indicative of product authenticity.

16. The warming system of claim 1, wherein the at least one operation includes activating the light source.

17. The warming system of claim 1, further comprising:
a sensor that measures physiological properties of a patient;
a computing device communicatively coupled to the sensor and comprising one or more computer processors and a memory comprising instructions that when executed by the one or more computer processors cause the one or more computer processors to:
receive the physiological property from the sensor;
determine a warming score based on the physiological property, wherein the warming score is indicative of a core body temperature of a patient;
determine whether the warming score meets a threshold;
perform at least one operation based on the warming score meeting the threshold.

18. The system of claim 17, wherein, to perform at least one operation, the memory comprises instructions that when executed by the one or more computer processors cause the one or more computer processors to provide instructions to the light device to change from a first heat setting to a second heat setting.

19. The system of claim 18, wherein the first heat setting includes activating a first set of bulbs for the light source and the second heat setting includes activating a second set of bulbs fewer than the first set of bulbs.

* * * * *